(12) United States Patent
Bazin et al.

(10) Patent No.: US 6,692,743 B1
(45) Date of Patent: *Feb. 17, 2004

(54) APOPTOSIS OF NAIVE HUMAN NK CELLS BY CROSSLINKING OF THEIR FCγRIIIA MOLECULES WITH A RAT IGG2B (LO-CD2A/BTI-322) OR ITS IGG1 HUMANIZED MONOCLONAL ANTIBODY

(75) Inventors: Herve Bazin, Brussels (BE); Dominique Latinne, Brussels (BE)

(73) Assignee: Universite Catholique de Louvain, Louvain-la-Neuve (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/305,128

(22) Filed: May 4, 1999

Related U.S. Application Data (60) Provisional application No. 60/084,885, filed on May 8, 1998.

(51) Int. Cl.$^7$ ........................ A61K 39/395; C07K 16/28
(52) U.S. Cl. .................. 424/154.1; 424/130.1; 424/133.1; 424/141.1; 424/143.1; 424/144.1; 424/153.1; 424/172.1; 424/173.1; 530/387.1; 530/387.3; 530/388.1; 530/388.15; 530/388.2; 530/388.7; 530/388.73; 530/388.75; 530/389.1; 530/389.6
(58) Field of Search ............................ 424/130.1, 144.1, 424/145.1, 153.1, 158.1, 173.1, 133.1, 141.1, 143.1, 154.1, 172.1; 530/387.1, 387.3, 388.1, 388.15, 388.2, 388.7, 388.73, 388.75, 389.1, 389.6

(56) References Cited

U.S. PATENT DOCUMENTS

| | | | |
|---|---|---|---|
| 5,730,979 A | | 3/1998 | Bazin et al. ............. 424/154.1 |
| 5,951,983 A | * | 9/1999 | Bazin et al. ............. 424/154.1 |

OTHER PUBLICATIONS

Sulica et al., Divergent Effects of Fc gamma RIIIA on the functional activities of NK cells, European Journal of Immunology, 26, pp. 1199–1203y, 1996.*

* cited by examiner

*Primary Examiner*—Anthony C. Caputa
*Assistant Examiner*—Anne L. Holleran
(74) *Attorney, Agent, or Firm*—Elliot M. Olstein; Raymond J. Lillie (57) ABSTRACT

Although the mechanism of induction of apoptosis through antibody dependent cellular cytotoxicity (ADCC) mediated by NK cells is well understood, little is known about the fate of the reactive NK cells. Nevertheless, it has been shown that NK cells previously activated by IL-2, but not naive NK cells, died by apoptosis after FcγRIIIa crosslinking, or after engagement in cytolytic functions. It is demonstrated that apoptosis of naive NK cells is also observed after stimulation with a rat IgG2*b* anti CD2 mAb (LO-CD2*a*/BTI-322) or anti HLAI (LO-HLA-1)mAb. The NK apoptosis is rapid (within minutes), Fas-ligand and mRNA synthesis independent and does not require a cell contact. The intracellular mechanism of NK cell apoptosis is calcium, PKC and PLA2 dependent but calcineurin and P13 kinase independent. We suggest that NK cell apoptosis results from the crosslinking on the same cell surface of CD2 or HLA-I molecules and FcγRIIIa that exhibits a high affinity for the rat IgG2*b* isotype. The clinical application of these experiments are discussed.

2 Claims, 6 Drawing Sheets

APOPTOSIS OF NAIVE HUMAN NK CELLS BY CROSSLINKING OF THEIR FCγRIIIA MOLECULES WITH A RAT IGG2B (LO-CD2A/BTI-322) OR ITS IGG1 HUMANIZED MONOCLONAL ANTIBODY

This application claims priority under 35 U.S.C. 119(e) based on provisional application Serial No. 60/084,885, filed May 8, 1998.

Natural killer cells (NK) play an important role in immune defenses by their capacity to kill tumour cells or infected cells through natural cytotoxicity or to kill antibody coated target cells by a mechanism referred as the antibody dependent cellular cytotoxicity (ADCC) (reviewed in 1) (Renard). This mechanism appears to involve crosslinking of the NK FCγRIIIa, rapid secretion of lytic factors (i.e., perforin/granzyme B) and expression of Fas-ligand which then triggers the apoptosis of targeted cells (2–9)(Vivier JI 91, Salcedo, Azzoni, Galandrini, Kanakaraj, Aramburu, Milella, Umera).

Although the mechanism of ADCC is well understood, little is known about the fate of the NK cells after the reaction and notably how the immune system regulates the activity of these cells functioning repeatedly after target cell lysis (10)(Ulberg). It was however recently demonstrated in vitro that some NK cells become inactivated and then died by apoptosis 24 to 48 hrs. after the ADCC reaction (11) (Jewett).

It has been demonstrated that Il-2 activated NK cells or LAK cells, but not naive NK cells undergo rapid apoptotic cell death after FcγRIIIa (12)(Orthaldo), CD94 (13)(Ida) or CD2 (14)(Ida) cross-linking with an antireceptor antibody, or after engagement in cytolytic functions (15)(Taga 1996). This activation induced cell death (AICD) of NK cells, that was suggested to contribute to the end of immune response, seemed to be dependent on the expression of Fas-ligand (16)(Eishen) or c-myc (17)(Azzoni).

In this application, it is described that apoptosis of freshly isolated NK cells occurs when the cells are treated in vitro with a mAb of which the Fc portion binds to their FcRγIIIa and the antigen binding specificity to some CD2 or HLA class I membrane molecules. This apoptosis occurs rapidly, does not require RNA synthesis and is Fas/Fas-ligand independent.

The invention now will be described with respect to the drawings.

FIG. 1

Purified NK cells ($10^6$/ml in 100 $\mu$l) were incubated with or without LO-CD2a (100 ng/ml final concentration). After a 3 h incubation, cells were PI stained or double labelled with anti CD2-FITC and anti CD56-PE mAbs and directly analysed by Facs (10000 cells) a) FL2 fluorescence of PI positive cells b) size (FSC) and granularity (SSC). PI positive dead cells are located in gate 1 (not shown) c) PI negative cells located in gate 2 were analysed by double fluoresence CD2–CD56. Results of one experiment is shown as representative of five.

FIG. 2

TUNEL labelling of NK cells incubated with LO-CD2a. $2 \times 10^4$ NK cells were incubated 5 H without (A) or with (B) LO-CD2a (100 ng/ml), collected on a slide by cytocentrifugation and DNA fragmentation determined by a TUNEL assay

FIG. 3

Kinetics of LO-CD2a mediated NK apoptosis. 100 $\mu$l of NK cells ($10^6$ cells/ml) isolated from blood of 3 different donors were incubated in triplicate with LO-CD2a (100 ng/ml) for different periods of time and cell death was analysed by flow cytometry after PI labelling. The mean of each triplicate is represented. The standard error of mean was less than 10%.

FIG. 4

LO-CD2a mediated apoptosis of isolated NK cells. 20 $\mu$l of NK cells ($10^5$ cells/ml) were loaded on a sterile plastic cell counting chamber and incubated at 37° C. in a Petri dish filled with X-VIVO 15 medium without (FIG. 4a) or with (FIG. 4b) LO-CD2a (100 ng/ml). After a 3 h incubation, trypan blue was added and cell mortality counted by lecture in optical microscopy.

FIG. 5

Cell surface expression of Fas and Fas ligand on a) naive or b) IL-2 stimulated NK cells. Freshly isolated or IL-2 stimulated (2 days with 200 U/ml 11-2) NK cells were labelled with DX2 (anti Fas) fluorescein labelled mAb, NOK-1 (anti Fas ligand) fluorescein labelled mAb, or MADNP-1 fluorescein labelled (istopye control) and analysed by flow cytometry.

FIG. 6

Effect of different inhibitors on LO-CD2a mediated NK apoptosis. 100 ul of freshly isolated NK cells ($10^6$/ml) were pre-incubated for 3 h at 37° C. in a 96 well plate with EGTA (20 mM), staurosporin (250 nM), quinacrine (10 mM), cyclosporin A (100 mg/ml), FK506 (100 mg/ml), wortmannin (500 ng/ml), concanamycin A (500 mM), cytochalasine D (1 mg/ml), actinomycin) (500 ng/ml final concentration), NOK-1 (25 mg/ml) or medium alone. After incubation for 3 hours with LO-CD2a (100 mg/ml final concentration) propidium iodide was added and cell mortality was analysed by flow cytometry. Each inhibitor was tested at different concentrations and the one giving the best inhibition without cytotoxicity was chosen.

The percentage of death cells was calculated as follows: 1−(% PI positive cells with LO-CD2a+inhibitor−% PI positive cells with inhibitor/% PI positive cells with LO-CD2a−% PI positive cells with inhibitor/×100. Results are the mean+SD of 5 experiments done with 5 different blood donors. The percentage of PI positive cells after incubation with the inhibitors alone never exceeded 20%.

MATERIALS AND METHODS

Antibodies and Reagents

A cell line which produces LO-CD2a, was deposited on Jul. 28, 1993, at the American Type Culture Collection, 12301 Parklawn Drive, Rockville, Md. 20852, and was given the ATCC accession number ATCC HB11423. Such antibody is a rat monoclonal antibody. Because the strain referred to is being maintained under the terms of the Budapest Treaty, it will be made available to a patent office signatory to the Budapest Treat.

LO-CD2a was purified from in vitro culture of ascites fluid. LO-CD2a is a rat IgG2b anti-human CD2 mAb developed and characterized as described previously in the Experimental Immunology Unit, Universityé Catholique de Louvain, Louvain La Neuve, Belguim. It is obtained from a rat hybridoma obtained by fusion of rat immunized spleen cells with the non-secreting 1R983F fusion cell line (18) (Bazin, 1982), (19)(Latinne), commercially developed for clinical use by Biotransplant Incorporated, Charlestown, Mass., USA and named BTI-322. LO-CD2b is also a rat IgG2b anti-human CD2 mAb recognizing a different epitope than that recognized by LO-CD2a. LO-HLAI-2 is a rat IgG2b mAb anti-human HLA class I. MARG2b-3 is a mouse IgG1 mAb anti rat IgG2b heavy chain. MARK-1 is a mouse IgG1 mAb anti rat kappa light chain MADNP-1 is a mouse IgG1 anti DNP mAb. These mAbs were all developed in our laboratory (20) (CRC). IR863 is a rat IgG2b monoclonal immunoglobulin produced by an immunocytoma tumour. (18)(Bazin). A humanized (IgG1) version of BTI-322 (humanized BTI-322) was obtained from Biotransplant Incorporated, Charlestown, Mass. USA.

The mouse 1 gG1 mAb anti human CD2, OKT11 (21) (VanWauve) and mouse IgG2a mAb, 35.1 (22)(Martin) were obtained from ATCC. The fluorescein-conjugated mouse anti human CD95 mAb, DX2 and anti Fas-ligand mAb, NOK-1, purified and fluorescein-conjugated were obtained from Pharmingen (Imtec, The Netherlands). NOK-1 mAb has been shown to neutralise the Fas-Fas-L mediated apoptosis (23)(Kayagaki). The fluorescein-conjugated mouse anti human CD2 mAb, Leu5b recognizing another epitope on the CD2 molecule than LO-CD2a (not shown) was purchased from Becton Dickinson (Erembodegem, Belgium). The phycoerythrin-conjugated mouse mAb anti human CD56, NKH1 was purchased from Coulter. LO-CD2a $F(ab^1)_2$, fragments were prepared by *Staphylococcus aureus* V8 proteinase digestion followed by gel filtration (24)(Rousseaux).

Staurosporine, Quinacrine, Wortmannin, Concanamycin A, Cytochalasin D and Actinomycin D were purchased from Alexis (Switzerland). Cyclosporin A (Sandoz, Belgium) and FK506 (Fujisawa, Japan) were provided by the hospital pharmacy.

Cell Isolation and Culture Conditions

Human PBMC were isolated from heparinized blood of healthy volunteers by gradient centrifugation on Ficoll Hypaque (LSM, International Medical, Belgium). Human CD56 positive cells were negatively selected from PBMC, using the StemSep NK cell enrichment kit with a cocktail of mAbs anti-glycophorin A, -CD3, -CD4, -CD14, -CD19 and -CD66b (StemCell Technologies Inc., Vancouver, Canada). More than 90% of isolated cells were CD56 positive and 90% of them were CD16 positive. The percentage of CD3 positive cells was within a range of 50 to 80%. Cells were suspended in X-VIVO 15 medium (Biowhittaker, Md., USA) and directly used. Experiments were performed using 100 µl of a suspension of $10^6$ cells per ml incubated at 37° C., 5% $CO_2$ in 96 well microplates (Nunc, Gibco, Belgium) with a predefined mAb concentration.

Immunofluorescence Analysis

Phenotypic analysis was performed using a FACscan cytofluorimeter and the data analysed using the Cell Quest program (Beckton Dickinson, San Jose, Calif., USA). PBS supplemented with 2% fetal calf scrum and 0.2% sodium azide was used as dilution medium for antibodies and washing solution for cells. $5 \times 10^5$ cells per tube were incubated with the different mAbs (5 µg/ml, final concentration) for 10 min at 20° C. The cells were washed and directly analysed.

Evaluation of Cell Death

Cell death was evaluated by optical microscopy and trypan blue exclusion, or by flow cytometry after propidium iodide labelling (5 µg/ml final concentration). Apoptosis was determined by collecting cells on a slide ($2 \times 10^4$ cells/slide) by a 5 min cytocentrifugation at $5 \times 10^4$ rpm (Cytospin2, Shandon, USA). The cytospins were fixed in 2% formalin (10 min RT), rinsed in PBS (5 min RT) and put in a plastic bag containing 200 ml of 0.01M buffer (S2031, Dako, USA) for microwave irradiation (6 min, 100W). Following this irradiation, slides were quickly immersed in PBS at RT for rapid cooling (10 min). Background was abolished by incubating the slides with normal sheep serum diluted 1/20 in PBS containing 5% BSA (30 min, RT). The TUNEL labelling kit was obtained from Boehringer Mannheim (TUNEL label N 1767291 and TUNEL enzyme N1767305 and TUNEL POD N1772465) and was used according to manufacter's instructions. Peroxidase activity was revealed by AEC+substrate kit (K3461, Dako; 5 min, RT) and finally, slides were rinsed, counterstained with Mayer's hematoxylin, washed under tap-water and mounted in an aqueous mounting medium (Faramount, Dako). Negative controls were obtained by omitting TdT (TUNEL enzyme) from the labelling mixture, all other steps being identical to the above protocol.

Evaluation of Cell Death in the Absence of Cell-cell Contact

Isolated cells ($10^5$/ml) were put into a γ irradiated plastic cell counting chamber (Glasstic slide 10. Hycor Biomedical Inc. California, USA). After confirmation of the absence of cell contact by optical microscopy, the cell counting chamber was placed in Petri dishes and incubated in 20 ml of X-VIVO 15 medium with or without LO-CD2a (100 ng/ml). After a 3 h incubation at 37° C., 5% $CO_2$, trypan blue was gently added with a needle in the chamber containing cells, and cell viability was determined by direct microscopic examination.

RESULTS

Apoptosis Induction of Freshly Isolated NK Cells

Figure 1A:
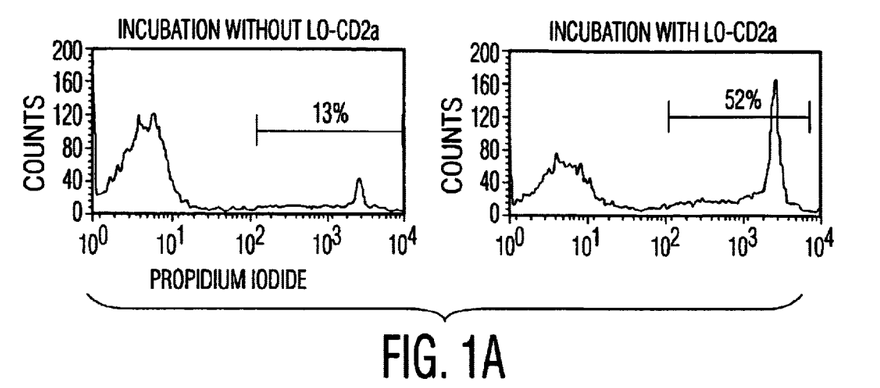
Figure 1B:
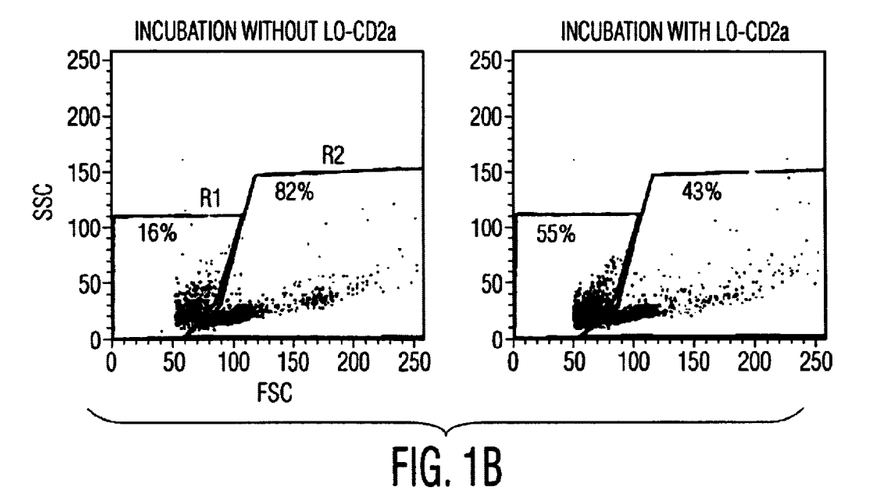
Figure 1C:
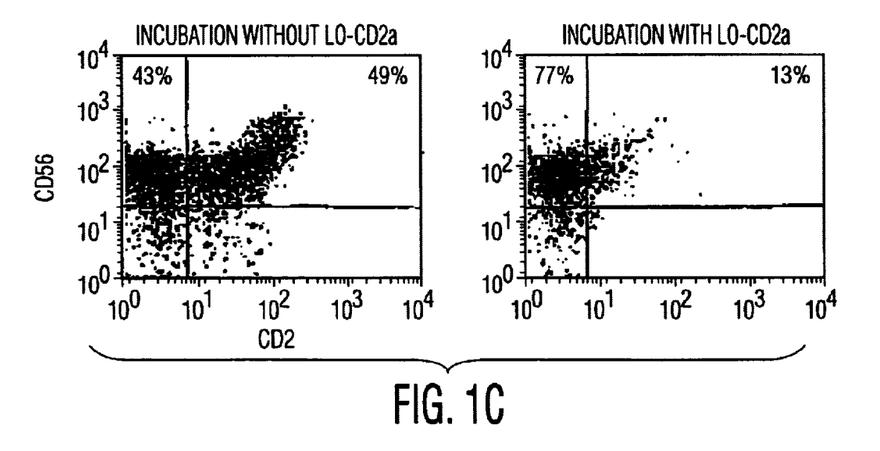

Freshly isolated NK cells were purified as described in material and methods. The mean±SD percentage of CD56+ CD2+ cells were 63±13 (n=5), a value similar to the one reported by Nakazawa (25)(Nakazawa) for naive NK cells. In the experiment described in FIG. 1, 60% of the cells were CD2 positive. After a 3 h incubation with or without LO-CD2a, cells were analysed by flow cytometry for viability after propidium iodide (PI) labelling (FIG. 1a), for size (FSC) and granularity (SSC) (FIG. 1b) and for CD2 and CD56 expression (FIG. 1c). The percentage of PI positive cells was 13% and 52% for cells incubated without and with LO-CD2a respectively (FIG. 1a). Cell death was also evaluated by optical microscopy after trypan blue staining. Results were similar to those obtained with PI labelling (not shown). These dead cells were located in the region 1 (R1) of the corresponding size/granularity dot plot (FIG. 1b). A double staining of residual living cells with anti-CD2 and anti-CD56 mAbs, located in the region (R2) showed an almost complete absence of the double positive population CD2+CD56+ in the sample treated with LO-CD2a (FIG. 1c).

Figure 2A:
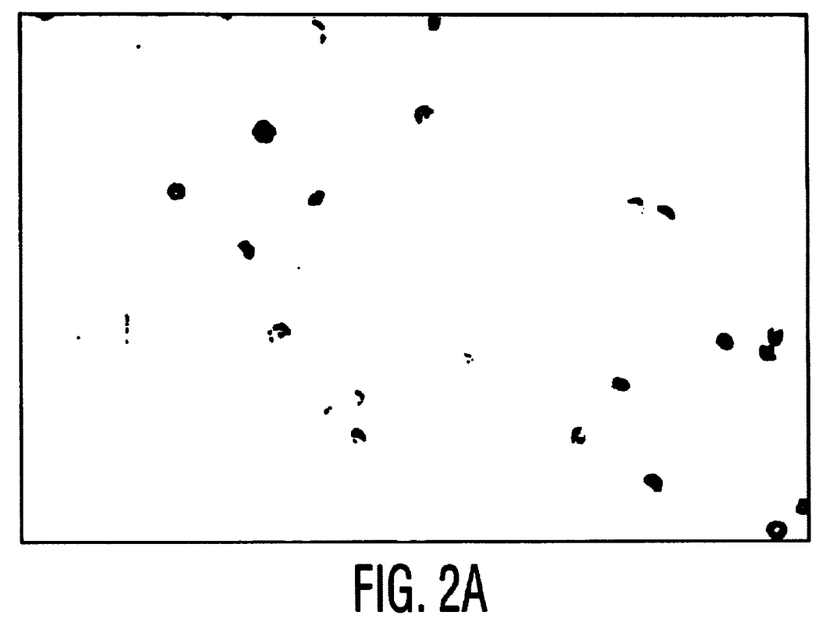
Figure 2B:
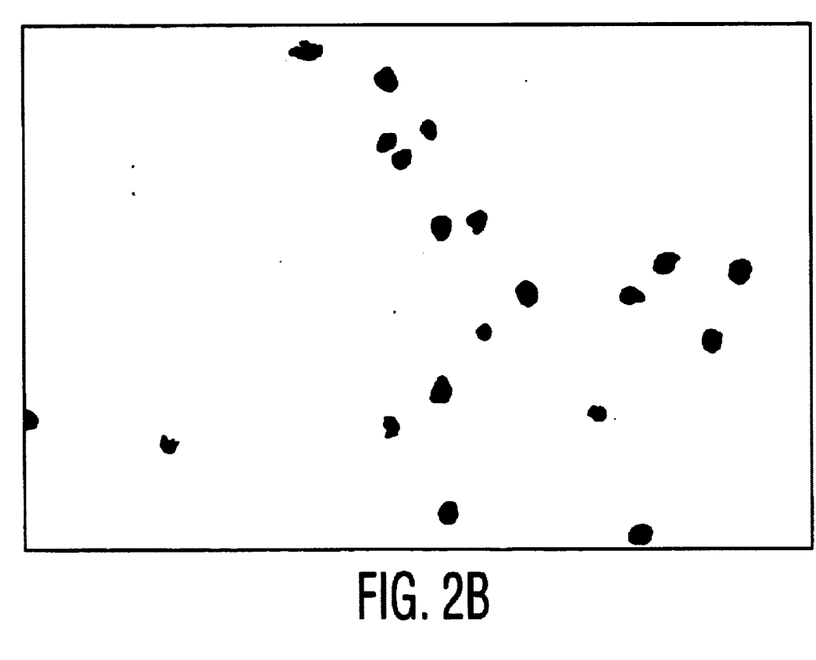

To determine if NK cells died following an apoptotic or a necrotic process, cells incubated with LO-CD2a were analysed by a TUNEL assay after cytocentrifugation (FIG. 2).

The percentage of TUNEL positive cells was similar to the one determined by trypan blue staining or propdium iodide labelling confirming that cells died by apoptosis (not shown).

Apoptosis of NK Cells Occurs Rapidly

Figure 3:
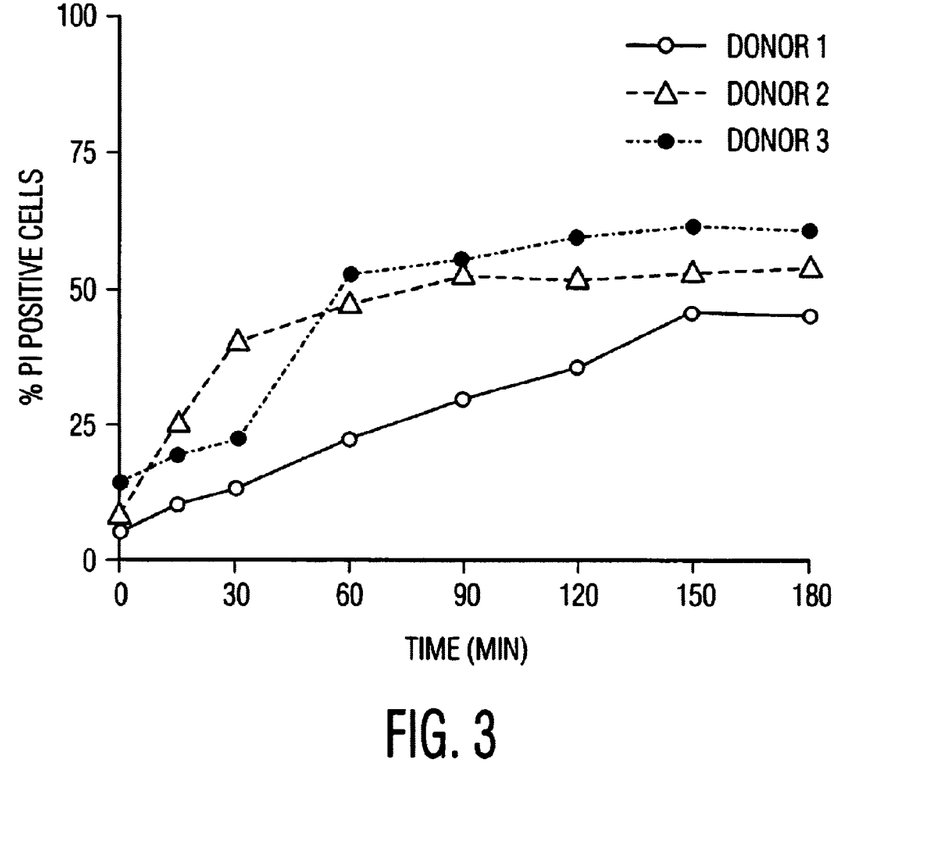

The kinetics of apoptosis was evaluated in 3 different donors by measuring the % of propidium iodide positive cells after different incubation times with LO-CD2a. Apoptosis was detected within 15 min and reached a maximal value between 60 and 150 min (FIG. 3).

Apoptosis is Neither Restricted to a Particular Epitope on the CD2 Molecule nor to the Rat IgG2b Isotype LO-CD2b, another rat IgG2b anti CD2 mAb that does not compete with LO-CD2a for CD2 binding and the humanized form of LO-CD2a with a human IgGi heavy chain induced a similar rate of apoptosis to the one observed with LO-CD2a (Table 1).

A Rat IgG2b Anti HLA Class I mAb Also Induces NK Apoptosis

The apoptosis, however, is not restricted to the CD2 recognition since the rat IgG2b anti HLA class I, LO HLAI 2 mAb induces apoptosis in 80% of NK cells (Table 1). The flow cytometry analysis of the residual alive cells showed that CD2+ and CD2− NK cells were equally sensitive to the LO-HLAI-2 mediated apoptosis (not shown).

Only the Whole Antibody is Able to Mediate Apoptosis

Apoptosis mediated by LO-CD2a cannot be induced by incubating cells with the LO-CD2a F(ab')$_2$ fragment with or without the control IgG2b IR863 monoclonal Ig and with or without the mouse anti-rat kappa chain (MARK-1) able to crosslink the LO-CD2a F(ab')$_2$ fragments (Table 1). The two mouse anti-human CD2 mAbs, OKT11 and 35.1, that were tested, also failed to induce apoptosis.

Apoptosis Does not Require a Cell-cell Contact

Figure 4A:
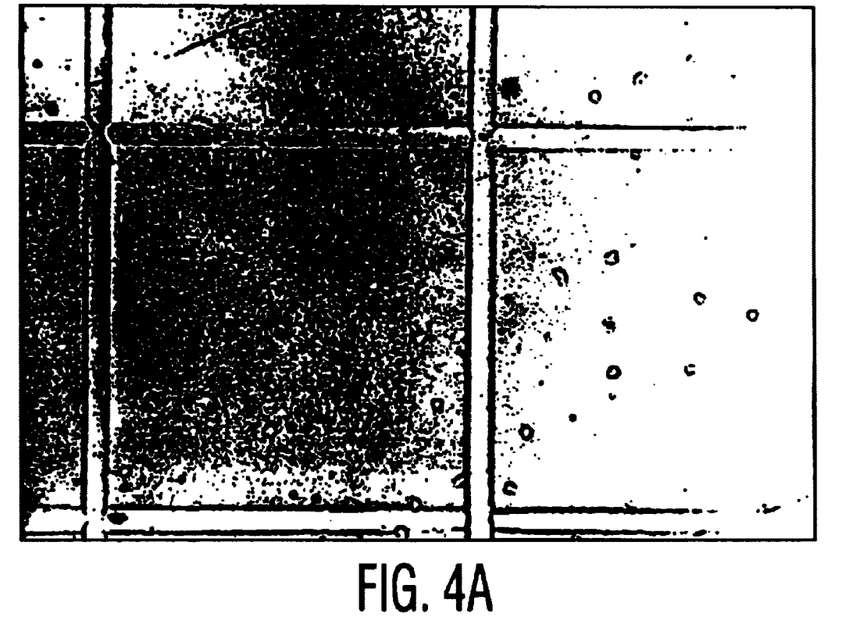
Figure 4B:
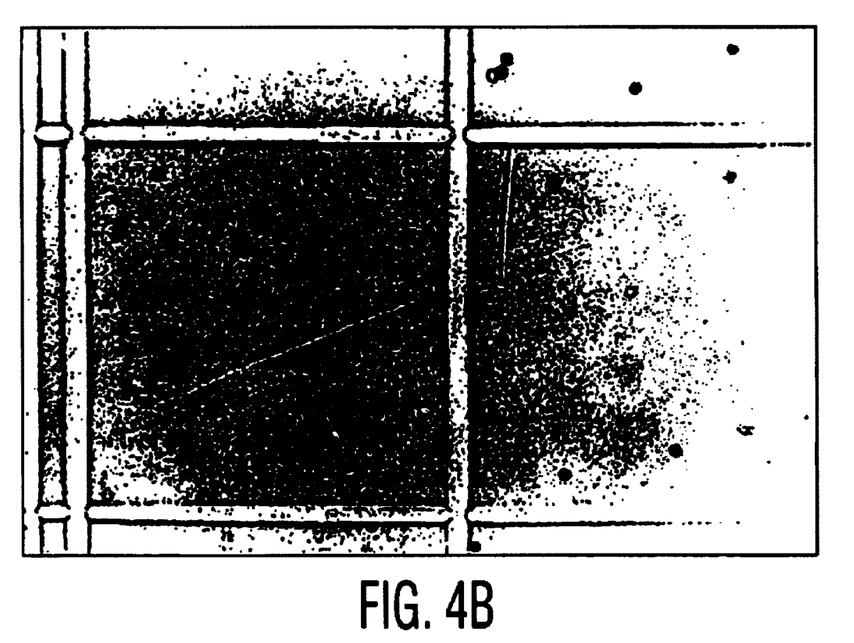

In order to determine if a cell contact was required for the LO-CD2a mediated apoptosis, cells at very low concentration were loaded on a cell counting chamber where they were clearly kept isolated and incubated in a LO-CD2a containing medium. After a 3 h incubation and trypan blue staining, cell mortality in the cell counting chamber (FIG. 4) was similar to the one observed or the same cells incubated with LO-CD2a in a 96 well plate (data not shown).

Apoptosis is Fas Ligand Independent

Figure 5A:
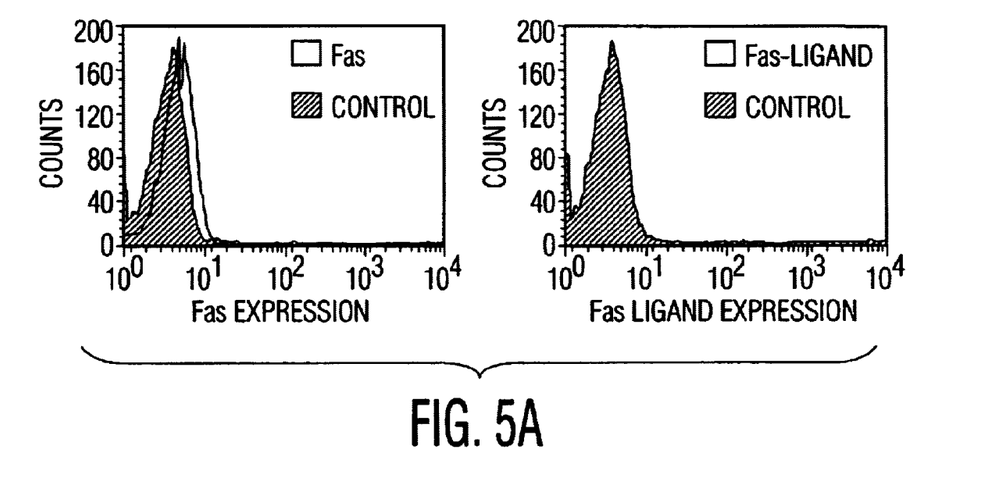
Figure 5B:
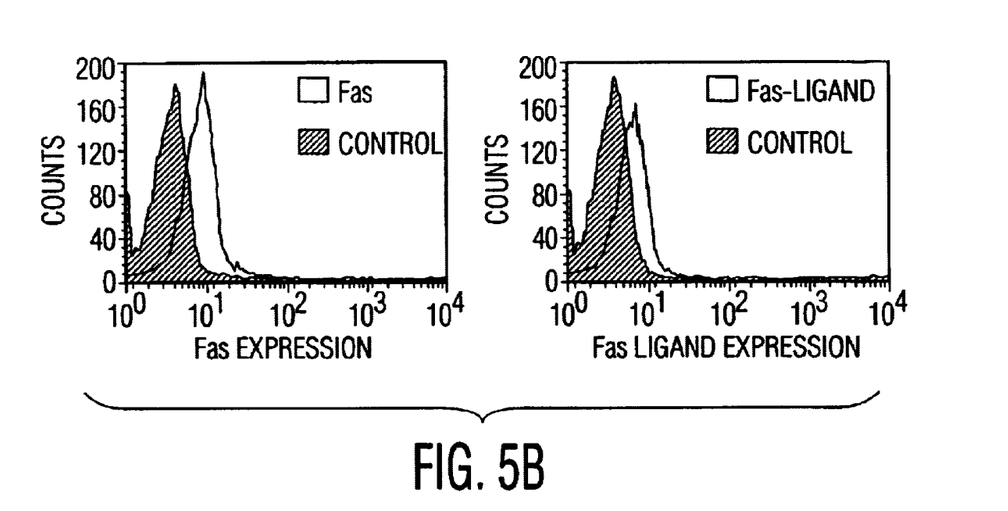

Purified NK cells express weakly Fas and no Fas ligand (FIG. 5A). As a control of Fas and Fas ligand expression, cells were incubated 2 days with IL-2 (200 U/ml). As previously described (16,26)(Ortaldo, Eishen), Fas ligand was expressed and the expression of Fas increased (FIG. 5B). To confirm that apoptosis of NK cells was not Fas-Fas ligand dependent, cells were also pre-incubated with the blocking anti Fas-L mAb, NOK-1. No inhibition of apoptosis was observed when LO-CD2a was added (FIG. 6).

Apoptosis is Calcium, PKC and PLA2 Dependent

Figure 6:
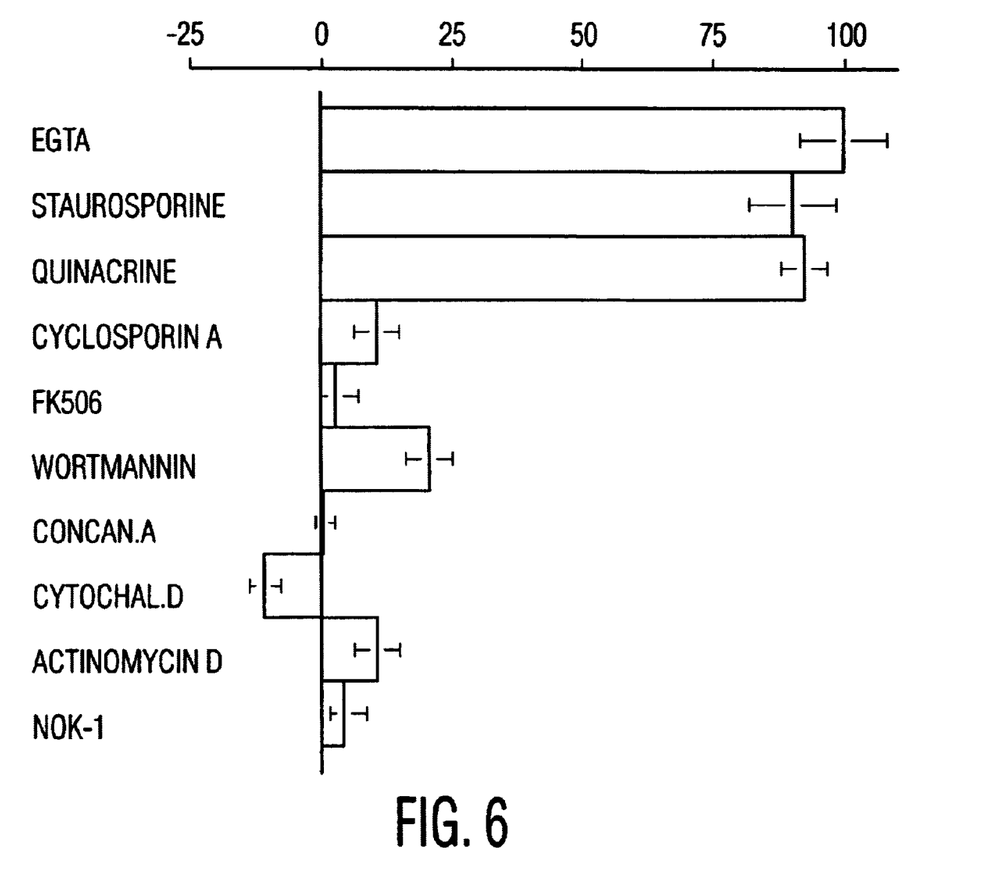

Several inhibitors were tested to determine the role of various mediators of apoptosis (FIG. 6). The calcium chelator, EGTA, as well as the PKC inhibitor staurosporine and the PLA2 inhibitor quinacrine, completely inhibited NK cell apoptosis. On the other hand, the calcineurin inhibitor, FK506, did not inhibit cell death, whereas high concentrations of cyclosporin A partially inhibited apoptosis. Wortmannin, inhibiting the PI3 kinase and blocking the degranulation, cytochalasine inhibiting microfilament formation, and concanamycin A, neutralising the perforin activity, failed to inhibit apoptosis. The inhibition of mRNA synthesis by actinomycin D, also did not have any blocking effect on apoptosis. Therefore, a role for calcium, protein kinase C and PLA2 in the apoptosis induced by LO-CD2a is hypothesized.

DISCUSSION

Until now, induction of NK cell apoptosis after FcγRIIIA cross-linking has been described only in cells previously activated by IL-2 (12,16,17) (Orlando, Azzoni, Eishen). In these experiments, IL-2 activation was thought to be required to start an apoptotic process triggered by a subsequent FcγRIIIa crosslinking. The increase of c-myc (17) (Azzoni) and Fas-ligand expression (16)(Eishen) by IL-2 was thought to be necessary for the FcγRIIIa mediated apoptosis. However, it has also been shown that neutralization of Fas ligand has no effect on NK cell AICD triggered by CD16 stimulation (14)(Ida). We show here that apoptosis of freshly isolated CD56+CD2+ NK cells also occurs when incubated with a rat IgG2b anti human CD2 mAb (LO-CD2a). We suggest that this mAb acts through the crosslinking of CD2 and FcγRIIIa. Indeed, it was shown that human FcγRIIIa exhibits a high affinity for the rat IgG2b isotype as high as for the human IgG1 (27,28,29) (Chassoux, Bruggemann, Hale).

The role of the rat IgG2b Fc portion was demonstrated by the failure of LO-CD2a F(ab')$_2$ fragments to induce apoptosis, even when crosslinked with a mouse anti rat kappa chain of the IgG1 isotype not able to bind human FcγRIIIa, whereas the role of the CD2 molecule was demonstrated by the absence of apoptosis of the CD2 negative NK cells.

The LO-CD2a mediated apoptosis is nevertheless not restricted to the binding of a particular CD2 epitope since another rat IgG2b anti human CD2, called LO-CD2b, binding another epitope than LO-CD2a, also induces NK apoptosis.

In order to exclude the hypothesis that apoptosis was due to a cytotoxic property of the rat IgG2b heavy chain, the humanized IgG1/kappa form of LO-CD2a, also was tested and showed the same apoptotic effect (Table 1).

In order to verify whether apoptosis was only due to FcγRIIIa stimulation or if CD2 costimulation also was necessary, a rat IgG2b anti human HLA class I (LO-HLAI-2) also was tested. This antibody induces up to 80% NK apoptosis regardless of CD2 expression. However, in this model, costimulation of the HLA class I molecules cannot be excluded completely since it was shown recently that HLA class I crosslinking on the cell surface also induces apoptosis of activated B and T cells (30)(Genestier).

The LO-CD2a mediated apoptosis is not only the result of a fratricidal ADCC reaction, since it occurs also when cells are kept separated.

As a result of these observations, it is suggested that the apoptotic process is triggered by the association of the CD2 or the HLA-1 molecule with the FcγRIIIa on the surface of the same cell through the binding of the Fab and Fc parts of the antibody.

Two mouse anti human CD2 mAbs were also tested. Neither OKTl1, a mouse IgG1 mAb, nor 35.1, a mouse IgG2a mAb were able to induce apoptosis, despite the fact that the mouse IgG2a Fc part can also bind to human FcγRIIIa (31)(Kipps). It has been reported that some mouse IgG2a are not able to bind efficiently the NK FcγRIIIa receptor and subsequently to trigger ADCC (32) (Christiaansen 84). The same authors have suggested later that the optimal stimulation of the FcγRIIIa might be dependent not only on the mAb isotype, but also on the spacial orientation of the mAb on the target cell membrane (33) (Christiaansen 90). The intracellular mechanism of apoptosis induced by LO-CD2a was investigated. It has been shown that stimulation of NK cells through their CD2 and the FcγRIIIa molecules induces an activation of i) PI-3 kinase (9,34)(Umehara, Bonema), ii) PKC and calcineurin through recruitment of p56 lck, p69 fyn or ZAP70 (3,4,35) (Salcedo, Azzoni, Vivier), iii) phospholipase A2 (PLA2) through the recruitment of Shc/Grb-2 and the Ras MAP kinase pathway (36)(Lin 93). These events trigger a rapid exocytosis of perforin/granzyme B containing granules and an activation of nucleic factors NFAT, NFkb, c-fos, c-jun, and c-myc that regulate the expression of INF-γ, TNFα and Fas ligand.

NK apoptosis produced by LO-CD2a is calcium dependent, as shown by its absence in presence of the calcium chelator, EGTA.

The occurrence of NK cell apoptosis through exocytosis of their own granules and the calcium dependent perforin activity seems unlikely since i) only CD2 positive NK cells are sensitive to the LO-CD2a mediated apoptosis; ii) neither the inhibition by wortmannin of the PI-3 kinase that regulates degranulation (34)(Bonema), nor the inactivation of perforin by concanamycin A (37)(Kataoka), nor the inhibition of exocytosis by cytochalasin are able to inhibit LO-CD2a mediated apoptosis.

The involvement of Fas ligand in the apoptotic process is unlikely since the cells used in the assays do not express Fas-L and the blockade of Fas/Fas-L interaction by the specific mAb, NOK1, fails to inhibit apoptosis.

Secretion of TNFα or overexpression of c-myc cannot be responsible for the induction of apoptosis since it occurs rapidly (apoptosis is already detected within 15 min) and without gene expression as shown by the inability of actinomycin D to prevent apoptosis.

The calcineurin pathway does not seem to be involved as demonstrated by the persistence of apoptosis in presence of the specific calcineurin inhibitors, FK506 and cyclosporin A.

The NK apoptosis is completely abrogated in the presence of the PKC inhibitor staurosporine as well as the PLA2 inhibitor, quinacrine. It has been suggested that PLA2 through production of arachidonic acid (AA) directly regulates the NK cell metabolism as well as the exocytosis of the granules (38)(Cifone). On the other hand, granzyme B have been also found outside the granules into the NK cells (39)(Trapani).

It may be possible that LO-CD2a, through a PLA2 pathway, induces an increase of cytosolic granzyme B/perforins as suggested by Spaner as an explanation of the Fas independent AICD of CD8+ cells triggered by TCR stimulation (40)(Spaner). The determination of the granzyme B location and the caspases activation, including the caspase 3 (CPP32) granzyme B substrate, is under investigation and will help to verify this hypothesis.

Ida et al (14) recently demonstrated that IL-2 primed, but not freshly isolated NK cells rapidly died by apoptosis after CD2 or CD16 stimulation with specific antibodies cross linked with a goat anti mouse Mab. The precise role of IL-2, that remains to be determined, was suggested to permit a link, via the CD3z recruitment, between the cytoplasmic domains of the receptors and the caspase cascade.

The NK apoptosis mediated by LO-CD2a is quite different as compared to that described previously with other antibodies, i.e., CD16 (26)(Orthaldo), CD94 (13) and CD2 (14)(Ida) since it does not require cross-linking with a second antibody nor priming with IL-2. Indeed, the cells used in our experiments were isolated from healthy volunteers and did not show any marker of IL-2 activation (i.e., absence of Fas-L and CD25 expression).

It might be possible that simultaneous triggering of CD2 and CD16 by LO-CD2a binding has the same effect as IL-2. Thus, it would be interesting to verify if the anti CD2 and anti CD16 Abs separately used by Ida to induce AICD of IL-2 primed NK cells, have the same effect as LO-CD2a, when added together on freshly isolated NK cells.

It has been suggested that NK cell depletion can be helpful in some clinical events such as allogeneic or xenogeneic graft rejection (41,42)(Blancho, Lin). The results presented in this paper demonstrate that a single rat IgG2b anti CD2 or HLA class I mAb can induce apoptosis of resting, even isolated NK cells. Anti CD2 treatment would fail to deplete CD2-NK cells, whereas anti HLA class I treatment could induce ADCC in different tissues expressing class I antigens. However, elimination of the whole NK cell population would be possible by using antibodies directed against a specific receptor restricted to NK cells such as the p46 molecule (43)(Sivori) and capable of binding by their Fc to the FcγRIIIa molecules.

TABLE 1

NK Apoptosis is Induced by Different Stimuli

100 μl of NK cells ($10^6$/ml) were incubated in triplicate with various mAbs at a concentration of 100 ng/ml, except for MARK-1 that was coated on the plate. This antibody also was used in a soluble form at various concentrations ranging from 10 ng/ml to 1 μg/ml and gave similar results (not shown). After a 3 H incubation, propidium iodide was added and cell mortality was analysed by flow cytometry. The results given above (mean+SEM) are representative of 5 experiments using different donors.

TABLE 1

| Stimulus | % PI Positive Cells |
| --- | --- |
| Medium | 11 ± 1 |
| LO-CD2a | 54 ± 4 |
| LO-CD2a Fab'2 | 12 ± 1 |
| LO-CD2a Fab'2 + MARK-1 | 13 ± 2 |
| IR863 | 10 ± 3 |
| IR863 + MARK-1 | 11 ± 2 |
| IR863 + LO-CD2a Fab'2 | 12 ± 3 |
| IR863 & Fab'2 + MARK-1 | 14 ± 4 |
| OKT11 | 9 ± 1 |
| 35.1 | 10 ± 1 |
| LO-CD2b | 56 ± 3 |
| Humanized LO-CD2a | 52 ± 2 |
| LO-HLA 1-2 | 80 ± 7 |

REFERENCES

1. Renard, V., A. Cambiaggi, F. Vely, M. Blery, L. Olcese, S. Olivero, M. Bouchet and E. Vivier, 1997, Transduction of cytotoxic signals in natural killer cells: a general model of fine tuning between activatory and inhibitory pathways in lymphocytes. *Immunol. Rev.*, 155:205–221.
2. Vivier, E., P. Morin, C. O'Brien, B. Drucker, S. F. Schlossman and P. Anderson. 1991. Tyrosine phosphorylation of the FcγRIIIa (CD16) complex in human natural killer cells: induction by antibody dependent cytotoxicity but not by natural killing. *J. Immunol.*, 146:206–210.
3. Salcedo, T. W., T. Kurosaki, P. Kanakaraj, J. Ravetch and B. Perussia. 1991. Physical and functional association of p56 lck with FcγRIIIa (CD16) in natural killer cells. *J. Exp. Med.*, 177:1475–1480.
4. Azzoni, L., M. Kamoun, T. W. Salcedo, P. Kanakaraj and B. Perussia. 1992. Stimulation of FcγRIIIa results in phospholipase Cγ1 tyrosine phosphorylation and p56 lck activation. *J. Exp. Med.*, 176:1745–1750.
5. Galandrini, R., P. Palmieri, M. Piccoli, F. Frati and A. Santoni. 1996. CD16-mediated p21 ras activation is associated with Shc and p36 tyrosine phosphorylation and their binding with Grb2 in human natural killer cells. *J. Exp. Med.*, 183:179–186.
6. Kanakaraj P., B. Duckworth, L. Azzoni, M. Kamon, L. C. Cantley and B. Prussia. 1994. Phosphatidylinositol-3 kinase activation induced upon FcγRIIIa-ligand interaction. *J. Exp. Med.*, 79:551–559.
7. Aramburu, J., L. Azzoni, A. Rao and B. Perussia. 1995. Activation and expression of the nuclear factors of activated T cells, NFATp and NFATc, in human natural killer cells: regulation upon CD16 ligand binding. *J. Exp. Med.*, 182:801–810.
8. Milella, M., A. Gismondi, P. Roncaioli, L. Bisogno, G. Palmieri, L. Frati, M. G. Cifone and A. Santoni. 1997. CD16 cross-linking induces both secretory and extracellular signal-regulated kinase (ERK)-dependent cytosolic phospholipase A2(PLA2) activity in human natural killer cells. *J. Immunol.*, 158:3148–3154.
9. Umera, H., J. Y. Huang, T. Kono, F. H. Tabassam, T. Okasaki, E. T. Bloom and N. Domac. 1997. Involvement of protein tyrosine kinase p72 syk and phosphatidylinositol 3-kinase in CD2-mediated granular exocytosis in the natural killer cell line, NK3.3. *J. Immunol.*, 159:1200–207.
10. Ullberg, M. and M. Jondal. 1981. Recycling and target binding capacity of human natural killer cells. *J. Exp. Med.*, 153:615–628.
11. Jewett, A., M. Cavalcanti, J. Giogi and B. Bonavida. 1997. Concomitant killing in vitro of both gp120-coated CD4+ peripheral T lymphocytes and natural killer cells in the antibody-dependent cellular cytotoxicity (ADCC) system. *J. Immunol.*, 158:5492–5500.
12. Ortaldo, J. R., R. T. Winkler-Pickett, N. Shigekazu and C. F. Ware. 1997. Fas involvement in human NK cell apoptosis: lack of a requirement for CD16-mediated events. *J. Leukocyte Biol.*, 61:209–215.
13. Ida, H., M. J. Robertson, S. Voss, J. Ritz and P. Anderson. 1997. CD94 ligation induces apoptosis in a subset of IL-2-stimulated NK cells. *J. Immunol.*, 59:2154–2160.
14. Ida, H. and P. Anderson. 1998. Activation-induced NK cell death triggered by CD2 stimulation. *Eur. J. Immunol.*, 28:1292–1300.
15. Taga, K., A. Yamauchi, K. Kabashima, E. T. Bloom, J. Muller and G. Tosato. 1996. Target induced death by apoptosis in human lymphokine activated natural killer cells. *Blood.*, 87:2411–2418.
16. Eischen, C. M., J. D. Schilling, D. H. Lynch, P. H. Krammer and P. J. Leibson. 1996 Fc receptor-induced expression of Fas ligand on activated NK cells facilitates cell-mediated cytotoxicity and subsequent autocrine NK cell apoptosis. *J. Immunol.*, 156:2693–2699.
17. Azzoni, L., I. Anegon, B. Calabretta and B. Perussia. 1995. Ligand binding to FcγR induces c-myc-dependent apoptosis in IL-2 stimulated NK cells. *J. Immunol.*, 154:491–499.
18. Bazin, H. 1982. Production of rat monoclonal antibodies with the LOU rat non-secreting IR983F myeloma cell line. In *Protides of the Biological Fluids*. H. Peeters, editor, Pergamon Press, Oxford and N.Y., 615–618.
19. Latinne, D., B. De la Parra, Y. Nizet, A. Cornet, V. Giovino-Barry, R. L. Monroy, M. White-Scharf and H. Bazin. 1996. An anti-CD2 mAb induces immunosuppression and hyporesponsiveness of CD2+ human T cell in vitro. *Int. Immunol.*, 8:1113–1119.
20. Bazin, H. 1990. Rat hybridoma and rat monoclonal antibodies. In *CRC Press*, Boca Raton, Fla.
21. Van Wauve, J., J. Goossens, W. Decock, P. Kung and G. Goldstein. 1981. Suppression of human T-cell mitogenesis and E-rosette formation by the monoclonal antibody OKT11A. *Immunology.*, 44:865–871.
22. Martin, P. J., G. Longton, J. A. Ledbetter, W. Newman, M. P. Braun, P. G. Beatty and J. A. Hansen. 1983. Identification and functional characterization of two distinct epitopes on the human T cell surface protein Tp50. *J. Immunol.*, 131:180–185.
23. Kayagaki, N., A. Kawasaki, T. Ebata, H. Ohmoto, S. Ikeda, S. Inoue, K. Yoshino, K. Okumura and H. Yagita. 1995. Metalloproteinase mediated release of human Fas ligand. *J. Exp. Med.*, 182:1777–1783.
24. Rousseaux, J., R. Rousseaux-Prevost, H. Bazin and G. Biserte. 1983. Proteolysis of rat IgG subclasses by *Staphylococcus aureus* V8 proteinase. *Biochim. Biophys. Acta.*, 748:205–211.
25. Nakazawa, T., K. Agematsu and A. Yabuhara, 1997. Later development of Fas ligand-mediated cytotoxicity as compared with granule-mediated cytotoxicity during the maturation of natural killer cells. *Immunology.*, 92:180–187.
26. Ortaldo, J. R., A. T. Mason and J. J. O'Shea, 1995. Receptor-induced death in human natural killer cells' involvement of CD16. *J. Exp. Med.*, 181:339–344.
27. Chassoux, D. M., L. G. Linares-Cruz, H. Bazin and M. Stanislawski, 1988. K-cell-mediated cytotoxicity induced with rat monoclonal antibodies. Antibodies of various isotypes differ in their ability to induce cytotoxicity mediated by rat and human effectors. *Immunology.*, 65:623–628.
28. Bruggemann, M., C. Teale, M. Clark, C. Bindon and H. Waldmann, 1989. A matched set of rat/mouse chimeric antibodies. Identification and biological properties of rat H chain constant region $\mu$, $\gamma$2a, $\gamma$2b, $\gamma$2c, $\epsilon$ and $\alpha$. *J. Immunol.*, 142:3145–3150.
29. Hale, G., M. Clark and H. Waldmann, 1985. Therapeutic potential of rat monoclonal antibodies: isotype specificity of antibody-dependent cell-mediated cytotoxicity with human lymphocytes. *J. Immunol.*, 134:3056–3061.
30. Genestier, L., G. Meffre, P. Garrone, J. J. Pin, Y. L. Liu, J. Bancherau and J. P. Revillard, 1997. Antibodies to HLA class I $\alpha$ 1 domain trigger apoptosis of CD40-activated human B lymphocytes. *Blood.*, 90:726–735.
31. Kipps, T. J., P. Parham, J. Punt and I. A. Herzenberg, 1985. Importance of immunoglobulin isotype in human antibody dependent, cell-mediated cytotoxicity directed by murine monoclonal antibodies. *J. Exp. Med.*, 161:1–17.
32. Christiaansen, J. E., S. S. Burnside and D. W. Sears, 1987. Apparent sensitivity of human K lymphocytes to the spacial orientation and organization of target cell-bound antibodies as measured by the efficiency of antibody-dependent cellular cytotoxicity (ADCC). *J. Immunol.*, 138: 2236–2243.
33. Christiaansen, J. E., and D. W. Sears, 1984. Unusually efficient tumor cell lysis by human effectors of antibody dependent cellular cytotoxicity mediated by monoclonal antibodies. *Cancer Res.*, 44:3712–3718.
34. Bonnema, J. D., L. M. Karnitz, R. A. Schoon, R. T. Abraham and P. J. Leibson, 1994. Fc receptor stimulation of phosphatidylinositol 3-kinase in natural killer cells is associated with protein kinase C-independent granule release and cell-mediated cytotoxicity. 180: 1427–1435.
35. Vivier E., P. M. Morin, C. O'Brien, S. F. Schlossman and P. Anderson. 1991. CD2 is functionally linked to the T-natural killer receptor complex. *Eur. J. Immunol.*, 21: 1077–1080.
36. Lin, L. L., M. Wartmann, A. Y. Lin, J. L. Knopf, A. Seth and R. J. Davis. 1993 cPLA2 is phosphorylated and activated by MAP kinase. *Cell.*, 72: 269–278.
37. Kataoka T., N. Shinohara, H. Takayama, K. Takaku, S. Kondo, S. Yonehara and K. Nagai. 1996. Concanamycin A, a powerful tool for characterization and estimation of contribution of perforin and Fas-based lytic pathways in cell-mediated cytotoxicity. *J. Immunol.*, 156: 3678–3686.
38. Cifone, M. G., P. Roncaioli, L. Cironi, C. Festuccin, A. Meccia, S. D'alo, D. Botti and A. Santoni, 1997. NKR-IA stimulation of arachidonate-generating enzymes in rat NK cells is associated with granule release and cytotoxic activity. *J. Immunol.*, 159: 309–317.
39. Trapani, J. A., M. J. Smyth, V. A. Apostolidis, M. Dawson and K. A. Browne. 1994. Granule serine proteases are normal nuclear constituents of nature killer cells. *J. Biol. Chem.*, 269: 18359–18365.
40. Spaner, D., K. Raju, L. Radvanyi, L. Yunping and R. G. Miller. 1998. A role for perforin in activation-induced cell death. *J. Immunol.*, 160: 2655–2664.
41. Blancho, G., F. Huselin, J. Dantal, M. Hourmant, D. Cantarovich, R. Baatard, M. Bonneville, H. Vie, L. Bugeon and J. P. Soulillou. 1992. Evidence that early acute renal failure may be mediated by CD3-CD16+ cells in a kidney graft recipient with large granular lymphocyte proliferation. *Transplantation.*, 53: 1242–1247.
42. Lin, Y., M. Vandeputte and M. Waer. 1997, Natural killer cell and macrophage mediated rejection of concordant xenografts in the absence of T and B cell responses. *J. Immunol.*, 158: 5658–5667.
43. Sivori, s., M. Vitale, L. Morelli, L. Sanaseverino, R. Augugliaro, C. Bottino, L. Moretta and A. Moretta. 1997. p46, a novel natural killer cell-specific surface molecule which mediates cell activation. *J. Exp. Med.*, 186:1129–1136.

What is claimed is:

1. A process for causing apoptosis of NK cells, comprising:
   contacting NK cells with an antibody which includes an Fc portion and which binds simultaneously (i) an epitope on NK cells selected from the group consisting of a CD2 epitope and an HLA class I epitope; and (ii) FcγRIIIa on NK cells.

2. The process of claim 1 wherein the NK cells are naive NK cells.

* * * * *